US010393414B2

(12) United States Patent
Johnson et al.

(10) Patent No.: US 10,393,414 B2
(45) Date of Patent: Aug. 27, 2019

(54) FLEXIBLE THERMAL REGULATION DEVICE

(71) Applicant: PALO ALTO RESEARCH CENTER INCORPORATED, Palo Alto, CA (US)

(72) Inventors: David Mathew Johnson, San Francisco, CA (US); Corie Lynn Cobb, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 236 days.

(21) Appl. No.: 14/578,212

(22) Filed: Dec. 19, 2014

(65) Prior Publication Data

US 2016/0178251 A1 Jun. 23, 2016

(51) Int. Cl.
| F25B 21/04 | (2006.01) |
| F25B 21/02 | (2006.01) |
| A41D 27/06 | (2006.01) |
| A61F 7/00 | (2006.01) |
| A61F 7/02 | (2006.01) |

(52) U.S. Cl.
CPC ............. *F25B 21/04* (2013.01); *A41D 27/06* (2013.01); *A61F 7/007* (2013.01); *A61F 7/02* (2013.01); *F25B 21/02* (2013.01); *A61F 2007/0075* (2013.01); *A61F 2007/0226* (2013.01); *A61F 2007/0244* (2013.01); *A61F 2007/0246* (2013.01); *F25B 2321/023* (2013.01); *F25D 2400/26* (2013.01)

(58) Field of Classification Search
CPC ...... F25B 21/04; F25B 2400/26; F25B 21/02; F25B 2321/023; F25D 2400/26; A41D 27/06; A61F 2007/0075
See application file for complete search history.

(56) References Cited

U.S. PATENT DOCUMENTS

| 3,554,815 | A |   | 1/1971  | Otto |
| 3,649,829 | A |   | 3/1972  | Randolph |
| 3,702,258 | A |   | 11/1972 | Gibbons et al. |
| 3,703,730 | A | * | 11/1972 | Miller ............... A41D 27/06 2/272 |
| 4,222,059 | A |   | 9/1980  | Crean et al. |
| 4,384,296 | A |   | 5/1983  | Torpey |
| 5,270,086 | A |   | 12/1993 | Hamlin |
| 5,386,701 | A | * | 2/1995  | Cao ............... A41D 13/0056 165/104.17 |
| 5,704,212 | A | * | 1/1998  | Erler ............... F25B 21/04 361/679.41 |

(Continued)

FOREIGN PATENT DOCUMENTS

EP 2227834 8/2011

OTHER PUBLICATIONS

Bhat, Pradeep P., "Formation of beads-on-a-string structures during break-up of viscoelastic filaments," Aug. 2010, vol. 6:625-631, Nature Physics, 7 pages.

(Continued)

*Primary Examiner* — David J Teitelbaum
(74) *Attorney, Agent, or Firm* — Miller Nash Graham & Dunn LLP

(57) ABSTRACT

A flexible temperature management device that uses powered thermoelectric elements to transfer thermal energy between a user and the environment to thermally regulate the user.

15 Claims, 15 Drawing Sheets

(56) References Cited

U.S. PATENT DOCUMENTS

| | | | | |
|---|---|---|---|---|
| 5,802,865 | A | * | 9/1998 | Strauss .............. A41D 13/0025 62/259.3 |
| 6,375,674 | B1 | * | 4/2002 | Carson .................. A61F 7/0085 5/422 |
| 6,576,861 | B2 | | 6/2003 | Sampath et al. |
| 6,840,955 | B2 | * | 1/2005 | Ein ......................... A61F 7/007 219/528 |
| 6,934,142 | B2 | | 8/2005 | Grosse et al. |
| 7,083,830 | B2 | | 8/2006 | Minko |
| 8,132,744 | B2 | | 3/2012 | King et al. |
| 8,272,579 | B2 | | 9/2012 | King et al. |
| 8,552,299 | B2 | | 10/2013 | Rogers et al. |
| 8,742,246 | B2 | | 6/2014 | Toyoda et al. |
| 2005/0000231 | A1 | | 1/2005 | Lee |
| 2009/0014046 | A1 | | 1/2009 | Yu et al. |
| 2010/0005572 | A1 | * | 1/2010 | Chaplin ................ A42B 3/285 2/411 |
| 2010/0154856 | A1 | | 6/2010 | Yuichi et al. |
| 2010/0198204 | A1 | * | 8/2010 | Rogers .................... A61F 7/007 606/21 |
| 2011/0017431 | A1 | | 1/2011 | Yang et al. |
| 2011/0150036 | A1 | | 6/2011 | Lee et al. |
| 2011/0154558 | A1 | | 6/2011 | Peter et al. |
| 2012/0227778 | A1 | | 9/2012 | Leonov |
| 2013/0087180 | A1 | | 4/2013 | Stark et al. |
| 2014/0109282 | A1 | * | 4/2014 | White ...................... A41D 1/00 2/69 |
| 2014/0146116 | A1 | | 5/2014 | Paschkewitz |
| 2014/0260331 | A1 | * | 9/2014 | Lofy ....................... F25B 21/02 62/3.3 |
| 2014/0352178 | A1 | * | 12/2014 | Bruce ..................... A43B 17/08 36/3 A |
| 2014/0352325 | A1 | * | 12/2014 | Brown .................... F25B 21/02 62/3.2 |
| 2015/0159812 | A1 | * | 6/2015 | Speer ..................... H05K 1/189 362/382 |
| 2015/0241092 | A1 | * | 8/2015 | Park ........................ F25B 21/04 62/3.2 |
| 2016/0161156 | A1 | * | 6/2016 | Nagesh ................... F25B 21/00 62/3.1 |

OTHER PUBLICATIONS

Le, Hue P., "Progress and Trends in Ink-jet Printing Technology," Jan./Feb. 1998, vol. 42:49-62, Journal Imaging of Science and Technology, 16 pages, found at http://www.imaging.org/ist/resources/tutorials/inkjet.cfm.

Oliveira, Monica S., "Iterated Stretching, Extensional Rheology and Formation of Beads-on-a-String Structures in Polymer Solutions," Jan. 20, 2006, Special Issue of JNNFM on Extensional Flow, MIT, Cambridge, MA, 36 pages.

Owen, M., "Misting of non-Newtonian Liquids in Forward Roll Coating," Jul. 13, 2011, Journal of Non-Newtonian Fluid Mechanics, vol. 166:1123-1128, 6 pages.

Shi, X.D., "A Cascade of Structure in a Drop Falling from a Faucet," Jul. 8, 2004, vol. 265:219-222, Science, 4 pages.

Chapter 15, "Ink Jet Printing", 14 pages, found at http://www.lintech.org/comp-per/15INK.pdf.

Marple, A. and Liu, Y.H.: "Characteristics of Laminar Jet Impactors", Environmental Sciene & Technology, vol. 8, No. 7, Jul. 1974, pp. 648-654.

Bailey, Adrian G.: "The Science and technology of electrostatic powder spraying, transport and coating", Journal of Electrostatics, vol. 45, 1998, pp. 408-416, URL: http://www.ppsc-journal.com.

Kelly, Ryan T, et al.: "The ion funnel: theory, implementations, and applications", Mass Spectrometry Reviews, vol. 29, 2010, pp. 294-312.

Crowe, Clayton et al.: "Multiphase Flows With Droplets and Particles", CRC Press, LLC, 1198.

Bullis, Kevin, "Expandable Silicon", MIT Technology Review, Dec. 14, 2007, URL: http://www.technologyreview.com/news/409198/expandable-silicon/, retrieved from the Internet on Dec. 23, 2014.

"Ortho-Planar Spring", BYI Mechanical Engineering Website, URL: http://compliantmechanisms.byu.edu/content/ortho-planar-spring, retrieved from the Internet on Dec. 23, 2014.

Kim, S-J, et al: "A wearable thermoelectric generator fabricated on a glass fabric," Energy Environmental Science, 2014.

Francioso, L., et al: "Wearable and flexible thermoelectric generator with enhanced package," In Proc. SPIE 8763, Smart Sensors, Actuators, and MEMS VI, 876306, May 2013.

Huizenga, et al: "Skin and core temperature response to partial-and whole-body heating and cooling," Journal of Thermal Biology, vol. 29, Issues 7-8, Oct.-Dec. 2004, pp. 549-558.

Sholin, V. et al.: "High Work Function Materials for Source/Drain Contacts in Printed Polymer Thin Transistors," Applied Physics Letters, vol. 92, 2008.

Zhou, Li, et al: "Highly Conductive, Flexible, Polyurethane-Based Adhesives for Flexible and Printed Electronics," Advanced Functional Materials, vol. 23, pg. 1459-1465, wileyonlinelibrary.com.

McClure, Max, "Stanford Researchers' Cooling Glove Better than Steroids—and Helps Solve Physiological Mystery Too", Stanford Report, Aug. 29, 2012, 3 pages, retrieved from the Internet: http://news.stanford.edu/news/2012/august/cooling-glove-research-082912.html, retrieved on Dec. 19, 2014.

Matheson, Rob, "Cool Invention Wins First Place at MADMEC", MIT News Office, Oct. 17, 2013, 3 pages, retrieved from the Internet: http://newsoffice.mit.edu/2013/madmec-design-competition-1017, retrieved on Dec. 19, 2014.

Vanhemert, Kyle, "MIT Wristband Could Make AC Obsolete", Wired.com, Oct. 30, 2013, retrieved from the Internet: http://www.wired.com/2013/10/an-ingenious-wristband-that-keeps-your-body-at-theperfect-temperature-no-ac-required/, retrieved on Dec. 19, 2014.

Francioso, L., "Flexible thermoelectric generator for ambient assisted living wearable biometric sensors", Journal of Power Sources, vol. 196, Issue 6, Mar. 15, 2011, pp. 3239-3243.

http://www.stacoolvest.com/, retrieved on Dec. 19, 2014.
http://www.steelevest.com/, retrieved on Dec. 19, 2014.
http://www.veskimo.com/, retrieved on Dec. 19, 2014.
http://www.glaciertek.com/, retrieved on Dec. 19, 2014.
http://www.cvs.com/shop/product-detail/CVS-Cold-Pain-Relief-Pack-Reusable?skuld=324111, retrieved on Dec. 19, 2014.

Chen, A.,"Dispenser-printed planar thick-film thermoelectric energy generators," J. Micromech. Microeng., 21(10), 2011.

Hewitt, A.B., "Multilayered Carbon Nanotube/Polymer Composite Based Thermoelectric Fabrics," Nano Letters, 12 (3), pp. 1307-1310, 2012.

Arens, E., "Partial- and whole-body thermal sensation and comfort—Part I: Uniform environmental conditions," Journal of Thermal Biology, vol. 31, Issues 1-2, Jan. 2006, pp. 53-59.

Arens, E., "Partial- and whole-body thermal sensation and comfort—Part II: Non-uniform environmental conditions," Journal of Thermal Biology, vol. 31, Issues 1-2, Jan. 2006, pp. 60-66.

\* cited by examiner

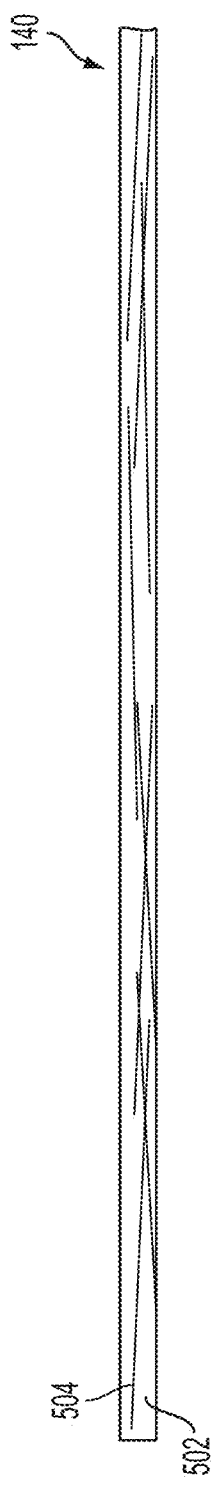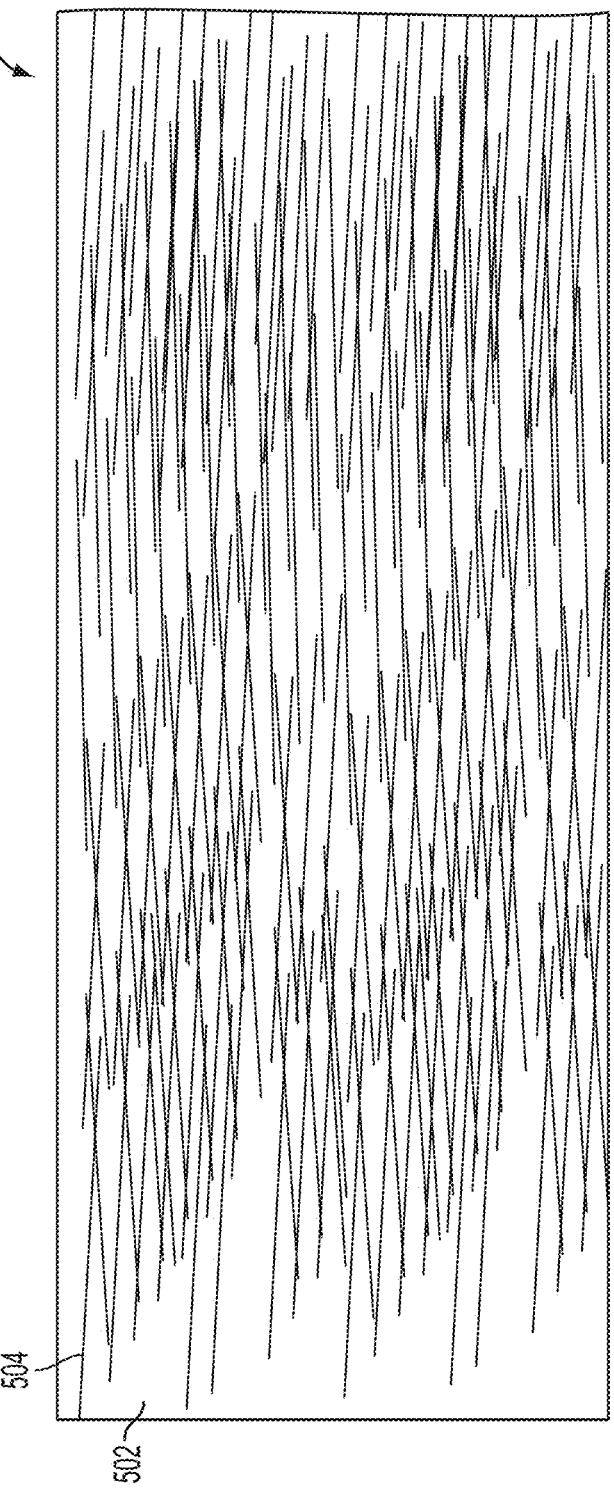

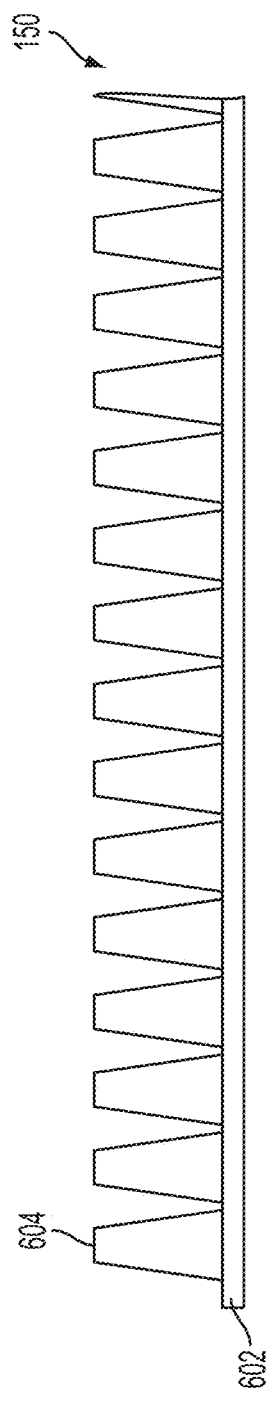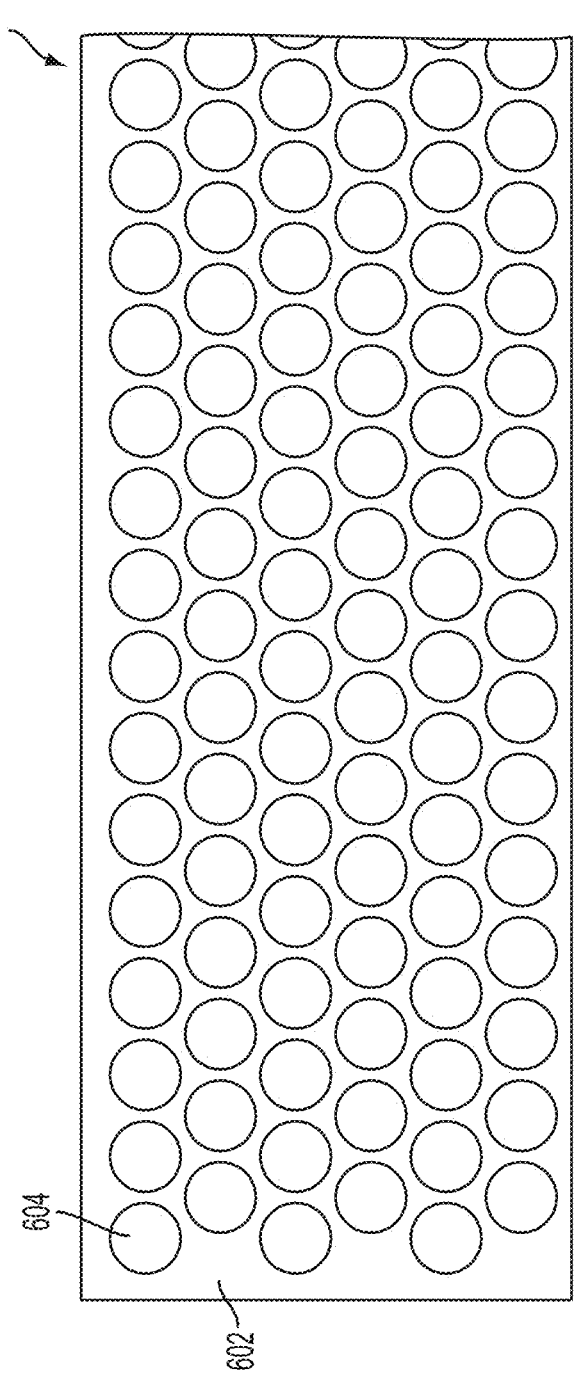

FLEXIBLE THERMAL REGULATION DEVICE

BACKGROUND

Humans are acutely attuned to changes in their surrounding temperature and often seek means to make themselves more thermally comfortable. A person's temperature regulation may be accomplished by modifying the temperature of the surrounding atmosphere, like HVAC systems, or by applying a thermal regulation device, such as an icepack or a heat pad, to the user themselves. The use of personal thermoregulation devices allows a user to try to achieve a desired level of thermal comfort without interfering with other people around them. Additionally, it is economical and desirable to allow a user to adjust their own thermal comfort, as each person's thermal tolerance varies.

One of the most common devices used for thermoregulation of body temperature is a "cool vest." These are vests that are worn by a user and absorb excess body heat, thereby keeping the user more comfortable. The vests may also serve a vital health role in ensuring a user's core temperature does not climb dangerously high as the user is performing a task in a hot environment. Such vests are often worn by surgeons in operating theaters, racecar drivers during races and other users who wish to maintain a comfortable or safe body temperature in an environment or while performing tasks. The cool vest may utilize either a passive or active cooling system. In the passive cooling form, the vest or inserts, such as gel ice packs, are chilled before being worn by a user.

As the vest is worn, the vest or inserts cools the user and help maintain user comfort and body temperature. The vests in a passive cooling form are limited in duration and ability to remove excess user heat since they lack a means to maintain their cool state. As the vest or inserts absorb a user's heat, they themselves start to warm up thereby lessening the cooling affect the user experiences. If the cooling means are in the form of the inserts, the inserts can be replaced as their efficacy wanes, but the user would be required to have access to pre-chilled inserts when replacement is necessary. Often the passive cooling vests are cheaper than active cooling vests since they are not required to have additional plumbing or wiring. In the active cooling form, the vest often features tubing through which a fluid may be circulated. As the fluid is circulated about the vest it absorbs body heat from the user, thus maintaining the user in a safe and/or comfortable temperature range. The fluid is often chilled and recirculated once it exits the vest. The need to rechill the fluid and provide recirculation means the vest needs to be connected to such equipment. Often this is an insulated vessel that has some sort of heat exchanger submerged in a cold fluid or a refrigeration type unit. The constant circulation of continuously chilled fluid about the vest keeps the user in a cool and comfortable state. The drawbacks of these active cooling vests are that they are typically bulky and may require additional resources, such as power, to function. These drawbacks limit the portability and deployability of such vests due to their required infrastructure.

Another active cooling device are cool gloves. These are small device in which users place their hand, which grips a metal cylinder. A vacuum is pulled in the chamber causing the blood vessels of the user's hand to come to the surface where they contact the cool metal cylinder. The contact between the cylinder and the user's hand cools the user's blood. The metal cylinder is kept cool by pumping chilled water through it. These devices are smaller and more portable than a cool vest but are still somewhat bulky. Additionally, the user is incapable of using their hand while using the device.

Another method of thermoregulation used by many people is the use of gel packs or other contained substances that can be chilled or warmed before applying. These are applied and held or restrained against the user's skin where the user experiences coolness or warmth. As these devices are used, their efficacy wanes as they either warm up or cool down due to the user's own body heat.

There exists a need for a user wearable device that provides the user thermal comfort, either by heating or cooling and does not hinder the user and their movements.

SUMMARY OF THE INVENTION

The invention is a flexible device having active thermoregulation abilities. The device has multiple layers, including an active thermal energy transfer layer, a thermal energy spreading layer and a thermal energy exchange layer. The active thermoregulation is accomplished by utilizing thermoelectric elements in an active thermal energy transfer layer. The thermoelectric elements are embedded in a graded material matrix that allows the overall device to be flexible, while allowing the thermoelectric elements to be rigid elements. The thermoelectric elements can generate heat or extract heat from a user. The extracted heat is then transferred to the thermal energy spreading layer where the thermal energy is then distributed across the layer and transferred to the thermal energy exchange layer. The thermal energy exchange layer transfers the thermal energy extracted from a user into the surrounding environment.

BRIEF DESCRIPTION OF DRAWINGS

FIG. 5A is a cross-section of an example thermal energy spreading layer.

FIG. 5B is a top view of the thermal energy spreading layer of FIG. 5A.

FIG. 6A is a side view of an example thermal energy exchange layer.

FIG. 6B is a top view of the thermal energy exchange layer of FIG. 6A.

DETAILED DESCRIPTION

The Active Thermal Regulation Device

Figure 1:
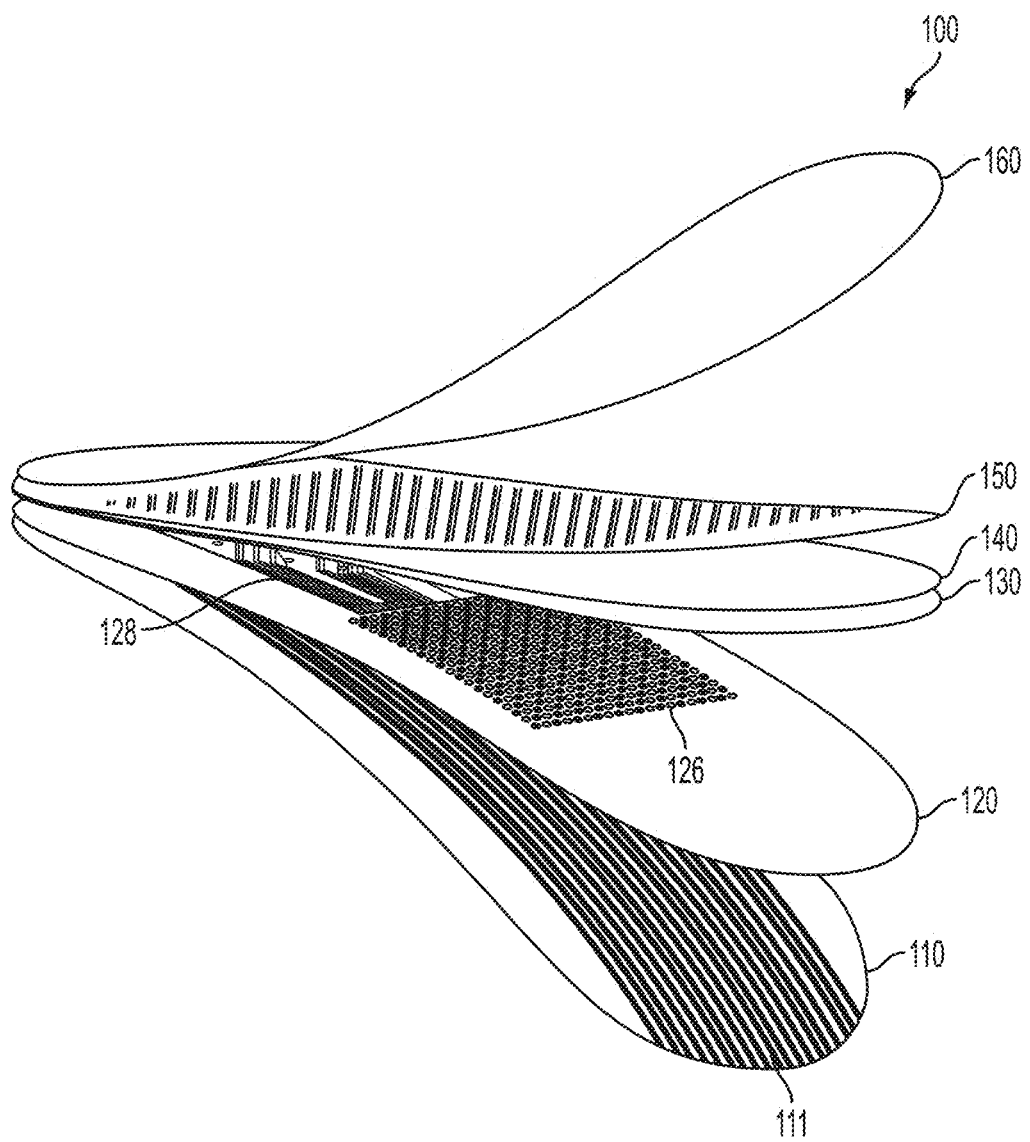
FIG. 1 is an exploded view of the active temperature control device showing the various layers of the device.

FIG. 1 shows the various layers of an embodiment of the active temperature control device 100. The bottom layer, the adhesive layer 110, has wicking elements 111 disposed thereon. The second layer, the thermal energy transfer layer 120, has thermoelectric elements 126 and power circuitry 128 disposed thereon. The third layer, a circuitry layer 130, contains a set of interconnects that electrically connect the thermoelectric elements 126 of the thermal energy transfer layer 120. The fourth layer, a thermal energy spreading layer 140, distributes thermal energy from the thermal energy transfer layer 120 throughout the thermal energy spreading layer 140. The fifth layer, a thermal energy exchange layer 150, dissipates energy from the thermal energy transfer layer 120 to the surrounding atmosphere. The sixth and top layer, a protective layer 160, encapsulates and protects the layers of the sticker from the surrounding environment. The protective layer can be conformal to the shape, contour, and flexibility of the other device layers and the user.

The device 100 is placed on a user's skin. The user's body heat is then drawn into the device by the thermal energy transfer layer 120. The thermoelectric elements in the thermal energy transfer layer 120 create a cool sink into which the user's body heat is drawn. The extracted heat is then distributed across the thermal energy spreading layer 140. From there, the heat is transferred into the thermal energy exchange layer 150 where it is dissipated into the surrounding environment.

One or more devices, 100, may be placed on a user to help regulate the user's body temperature.

Figure 2A:
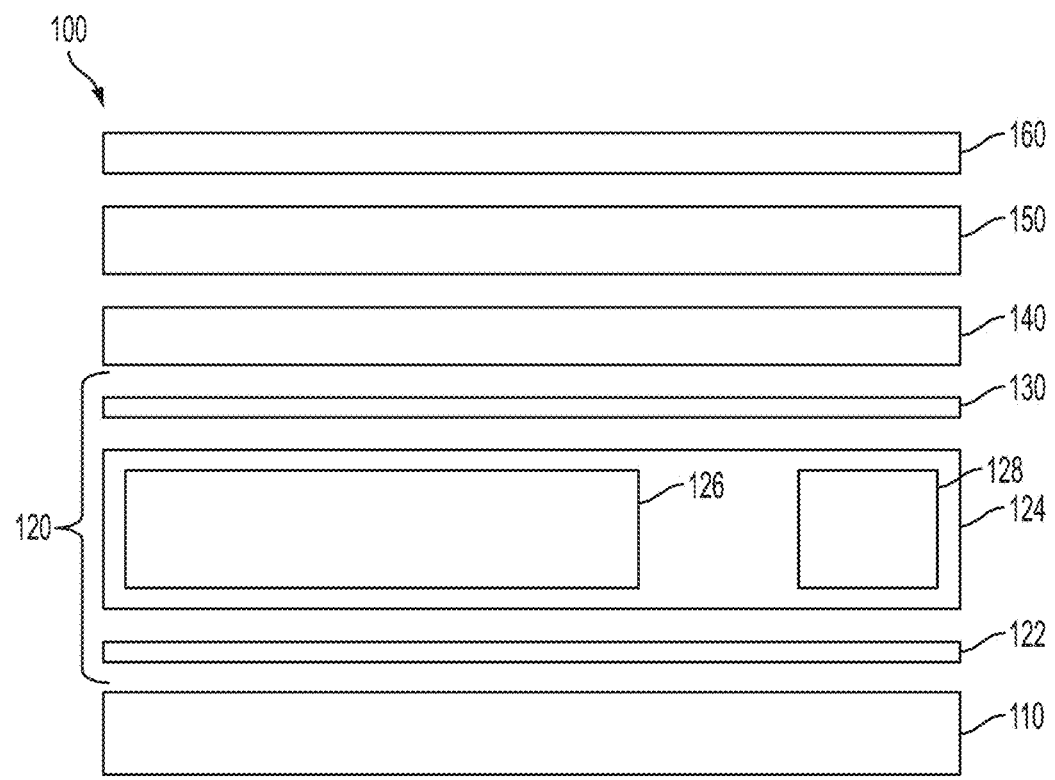
FIG. 2A is a cross-section of the example device shown in FIG. 1.

A cross-section of the device 100 and its layers are shown in FIG. 2A. The thermal energy transfer layer 120 has sub-layers: an interconnect layer 122 and a functionally graded material layer 124 that includes the thermoelectric elements 126 and the power circuitry 128.

Figure 2B:
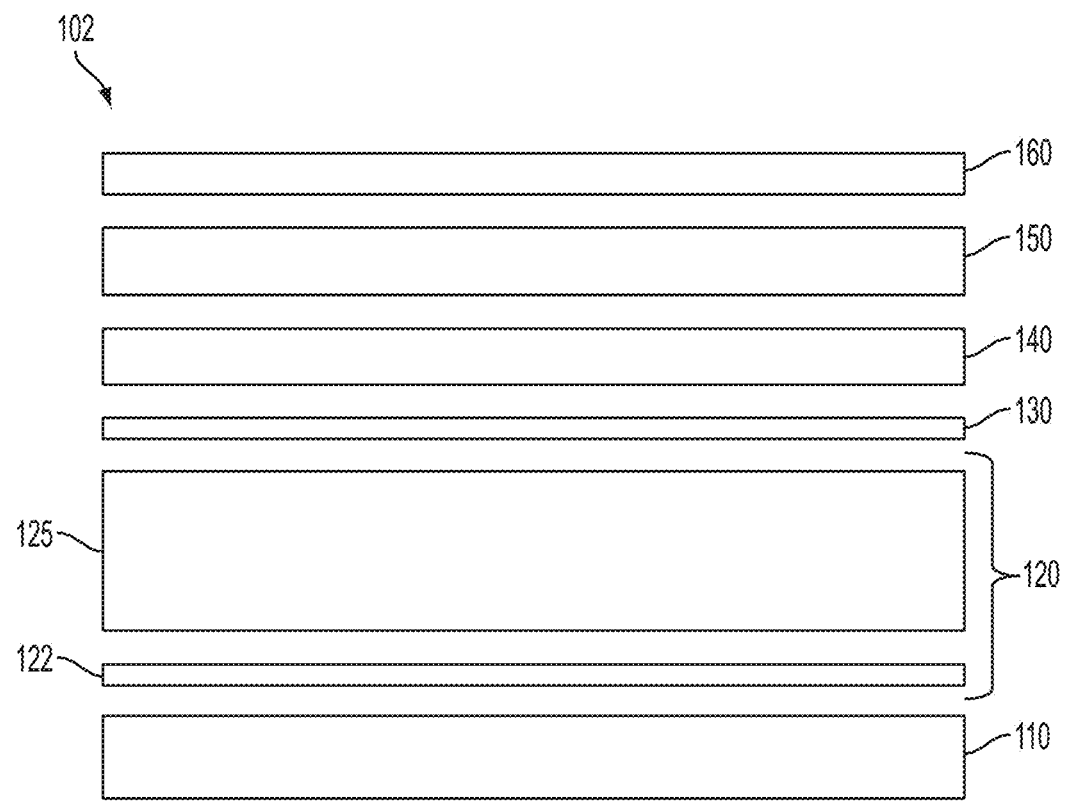
FIG. 2B is a cross-section of a second embodiment of the device.

In an alternative embodiment as shown in FIG. 2B, the device 102 layers are similar to the device in FIG. 1. In this embodiment, the thermoelectric elements and functionally graded material are integrated into a single layer 125. In this embodiment, the individual thermoelectric elements may have their own power circuitry or may be powered by an external power source. This arrangement of the thermoelectric elements may reduce or eliminate the need for on-device power circuitry as shown in the embodiment of FIG. 2A.

Figure 2C:
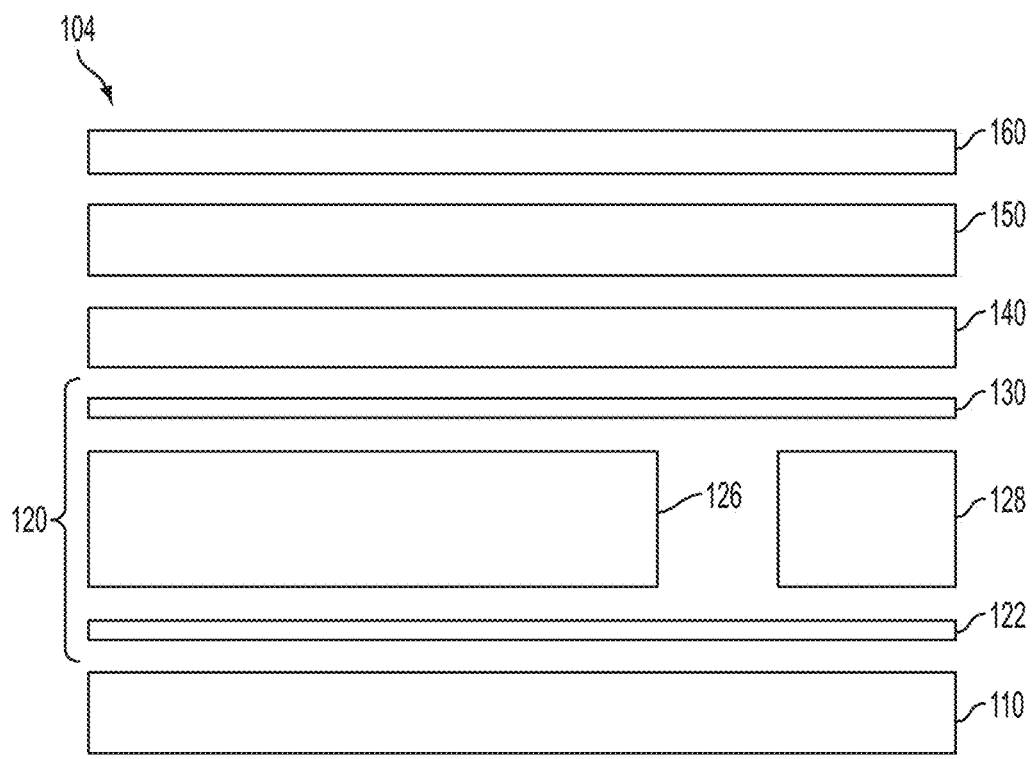
FIG. 2C is a cross-section of a third embodiment of the device.

In another alternative embodiment as shown in FIG. 2C, the device 104 is similar to the device of FIG. 1. In this embodiment, the first interconnect layer 122, the thermoelectric elements 126 and the power circuitry 128 compose the thermal energy transfer layer 120. Rather than placing the thermoelectric elements 126 and power circuitry 128 in functionally graded material as shown in the previous embodiments of FIGS. 2A and 2B, the thermoelectric elements 126 and power circuitry 128 are discrete elements that are placed in the device. The discrete elements 126 and 128 contain functionally graded material about the thermoelectric elements and power circuitry to enable each to flex.

The device 100 contains thermoelectric elements that actively cool or heat the user. The thermoelectric elements use the Peltier Effect to affect temperature change. The Peltier Effect occurs when current is passed through a junction between two different conductors. The flow of current causes the junction to either gain or lose heat depending on the directions of the current flow. Two conductors, a N-type and a P-type, are in contact with each other, and current is passed through them. As the current flows through the conductor pair, so does the heat, as one side of the conductor pair cools down and the other side heats up.

The thermoelectric element conductors can be composed of thermoelectric material such as Bismuth chalcogenides and others. Multiple conductors can be arranged thermally in parallel and/or electrically connected in series to increase their thermal capabilities. Thermoelectrics do not have any moving parts. Therefore, maintenance is minimal and the working life span of such devices is extended.

Functionally graded material (FGM) is a material that has varying mechanical properties across its dimensions. In the case of the device 100, the FGM has varying strain properties, meaning that the stiffness or rigidity of the material is varied. The FGM surrounds the rigid thermoelectric elements (TEs) to form a matrix that is stiffer around the TEs and gradually gets less so away from the TEs. The mechanical properties of the FGM are capable of being modified to desired levels during the manufacturing process.

Thermal Energy Transfer Layer

Figure 3A:
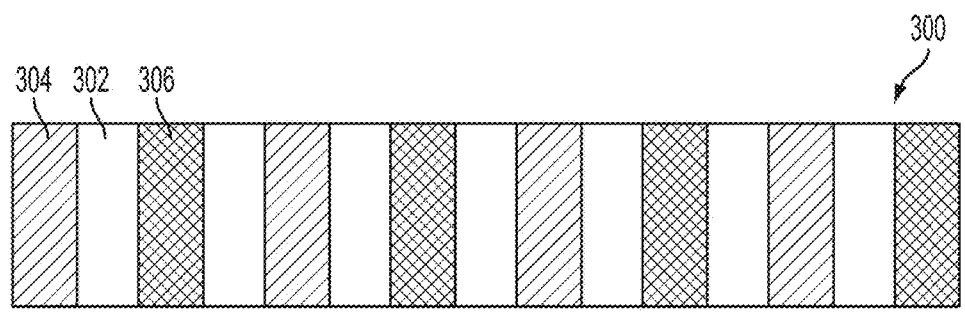
FIG. 3A is a cross section of example thermoelectric elements of the device.
Figure 3B:
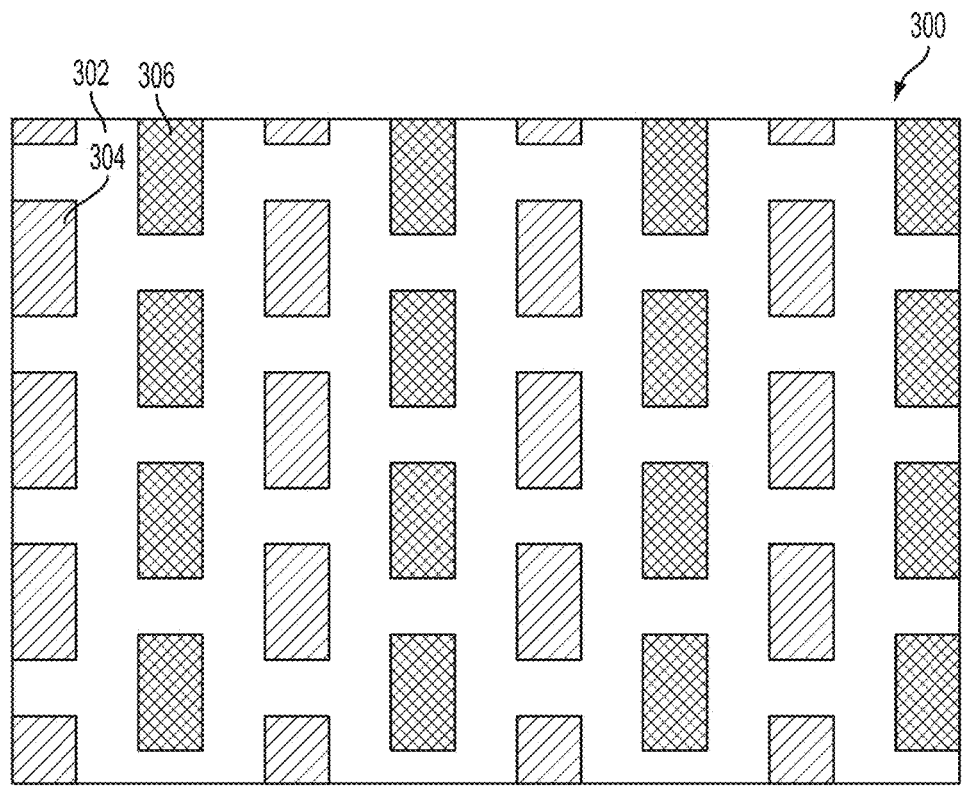
FIG. 3B is a top view of the thermoelectric elements of FIG. 3A.

The thermoelectric elements (TEs) in the functionally graded material (FGM) matrix of the thermal energy transfer layer 300 are shown in FIGS. 3A and 3B. P-type conductor material 304 and N-type conductor material 306 are disposed in the FGM matrix 302. The conductor material, 304 and 306, are arranged in parallel rows and spaced in an alternating pattern as shown in FIG. 3B.

The conductor materials 304 and 306, as shown in FIG. 3B, are each rectangularly shaped, but may be alternate shapes such as round or other shapes as desired. Alternatively, the conductor materials may have different shapes. It may be desirable to have alternatively shaped conductor material depending on the desired mechanical properties for the layer.

Figure 4A:
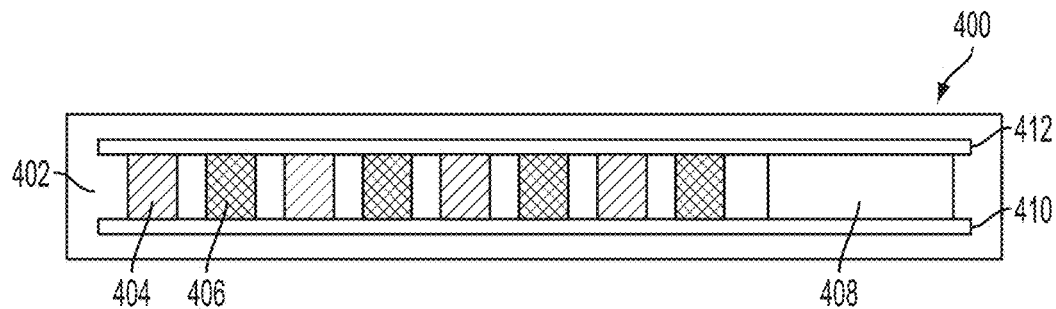
FIG. 4A is a cross-section view showing example power circuitry, connection circuitry and the thermoelectric elements.
Figure 4B:
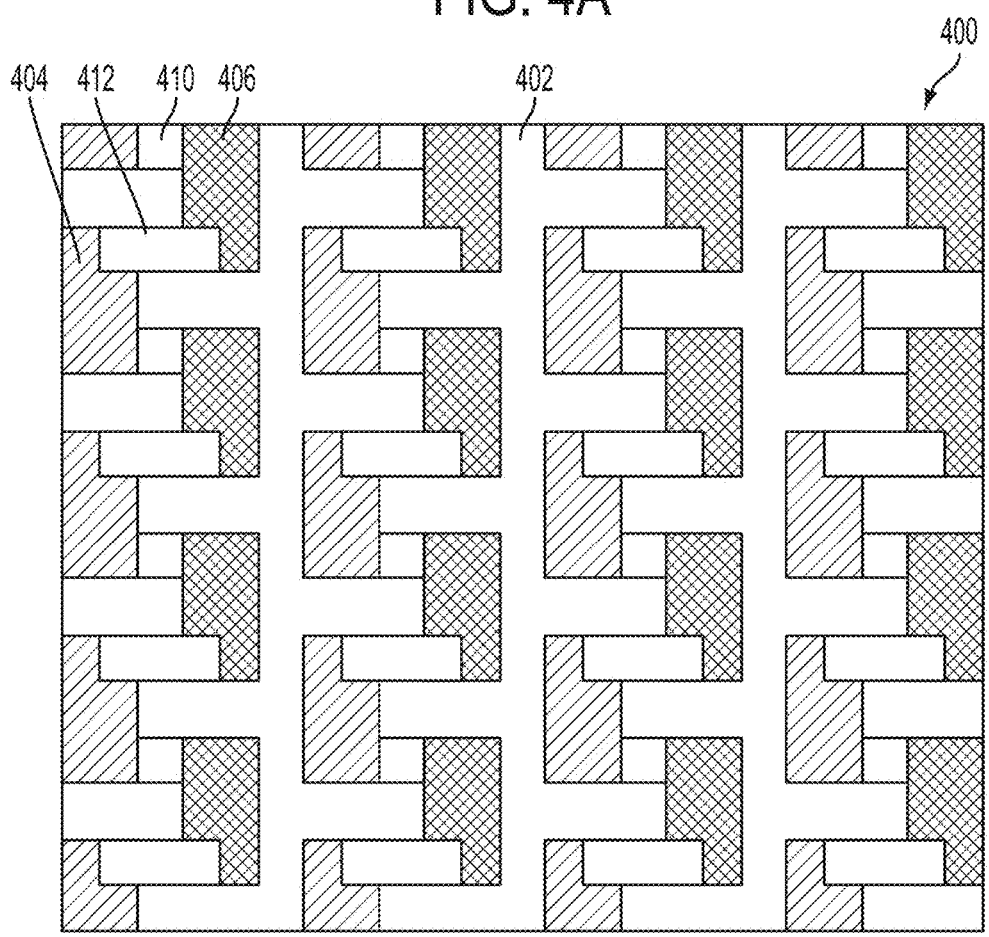
FIG. 4B is a top view of example connections between the thermoelectric elements.

The TEs, 404 and 406, are shown disposed between the two interconnects, 410 and 412, in FIG. 4A. FIG. 4B shows the TEs, 404 and 406, of FIG. 4A in a top view, showing the details of the interconnects 410 and 412. The first interconnect 410 connects the bottom portions of the p- and n-type conductor materials 404 and 406 of the TEs. The second interconnect 412 connects the top portion of the TEs. As shown in FIG. 4B, the TEs 404 and 406 are connected in a staggered fashion, i.e., the TEs 404 and 406 are connected in series. Further, the connections between the elements 404 and 406 are staggered vertically between the first and second interconnects. The vertically staggered series connection pathways between the TEs 404 and 406 create the hot and cold side of the thermoelectric elements. The direction of current flow through the array of TEs determines whether the top or bottom side is the cold side. With the cold side towards the user's skin, the TEs function as a heat sink, removing thermal energy from the user.

FGM 402 surrounds the TEs, as shown in FIG. 4A. The FGM allows the layer 400 to flex without disrupting the interconnects 410 and 412 and minimizes the strain, induced by flexing the layer, into the individual TEs. The interconnects 410 and 412 are also flexible and ideally are strain matched to the TEs, 404 and 406, and the surrounding FGM 402. By strain matching the various components, the layer can flex and bend without dislodging the components and connections.

Power circuitry 408 is disposed in the layer 400 and is connected to the interconnects 410 and 412 to power the TEs 404 and 406. The power circuitry 408 is also constructed in manner to maintain the flexibility of the layer 400. In this embodiment, a flexible polymer base is constructed with disposed interconnects. It may be preferred to have the interconnect base be strain matched to the TEs disposed thereon, i.e., the base is stiffer where the TEs are located.

Thermal Energy Spreading Layer

An embodiment of the thermal energy spreading layer 140 is shown in FIGS. 5A and 5B. Flexible thermal energy spreading elements 504 are disposed in a flexible matrix 502. In the embodiment shown, the thermal energy spreading elements 504 are thermally conductive traces that are printed onto the matrix material 502. Alternatively, thermal energy spreading elements 504 may be thermally conductive structures that are then suspended in the matrix 502. The matrix 502 may be FGM or other strain suitable material. The thermally conductive structures disposed on the layer spread the heat transferred from the thermal energy transfer layer 120 across the layer 140. The spread of thermal energy enlarges the area through which the heat may then be transferred to the thermal energy exchange layer 150. The increased thermal transfer capacity through the layer allows for greater efficiency in dissipating the heat from the user.

Alternatively, the heat spreading layer can have a flexible heat pipe structure, not shown. A heat pipe is a sealed device containing a liquid that is readily vaporized into a gas. The gas then expands to fill the device, thereby increasing the surface area of the gas available for thermal energy transfer. In the device 100, the heat pipe is a flexible structure, able to bend and flex with the device without damaging the structure. As thermal energy is transferred from the thermal energy transfer layer 130 into the flexible heat pipe of the thermal energy spreading layer 140, the gas within the heat pipe heats. The heated gas then flows evenly throughout the heat pipe, thereby spreading the thermal energy over a large area. The thermal energy of the gas can then be transferred to the next layer, the thermal exchange layer 150.

Ideally the strain properties of the layer 140 should match the strain properties of the other layers in the device. Strain matching assists in maintaining the overall structure of the device 100 when the device 100 is flexed.

Thermal Energy Exchange Layer

An embodiment of the thermal energy exchange layer 150 is shown in FIGS. 6A and 6B. The layer 150 consists of a conductive polymer base 602, which receives thermal energy from the thermal energy spreading layer 140. The thermal energy is then transferred into thermal dissipating structures 604. The vertical configuration of the structures 604 increases the surface area through which the heat may be convected away from the thermal energy exchange layer 150. In the embodiment shown, the structures 604 are filled with a thermally conductive polymer. By using thermally conductive materials, the user's heat is more efficiently transferred through the device 100 and evacuated by the thermal energy exchange layer 150. The dissipating structures 604 can be formed, by a process such as injection molding or other suitable means. Alternatively, the structures may be placed on or created in-situ on the base layer 602. Further, the base 602 and 604 may be the same thermally conductive material with the structures 604 later formed thereon using a forming process. Other structure 604 designs exist and may be utilized as needed. The amount of heat to dissipate and the manufacturing process used may determine the design of the structures 604.

Adhesive Layer

Figure 7A:
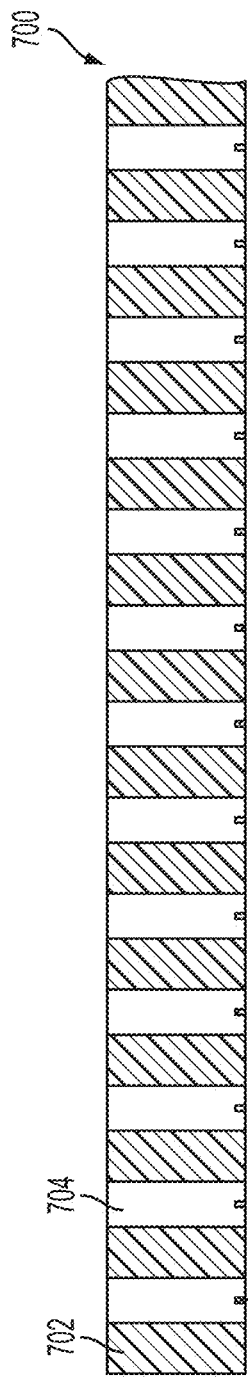
FIG. 7A is a cross-section view of an example adhesive layer.
Figure 7B:
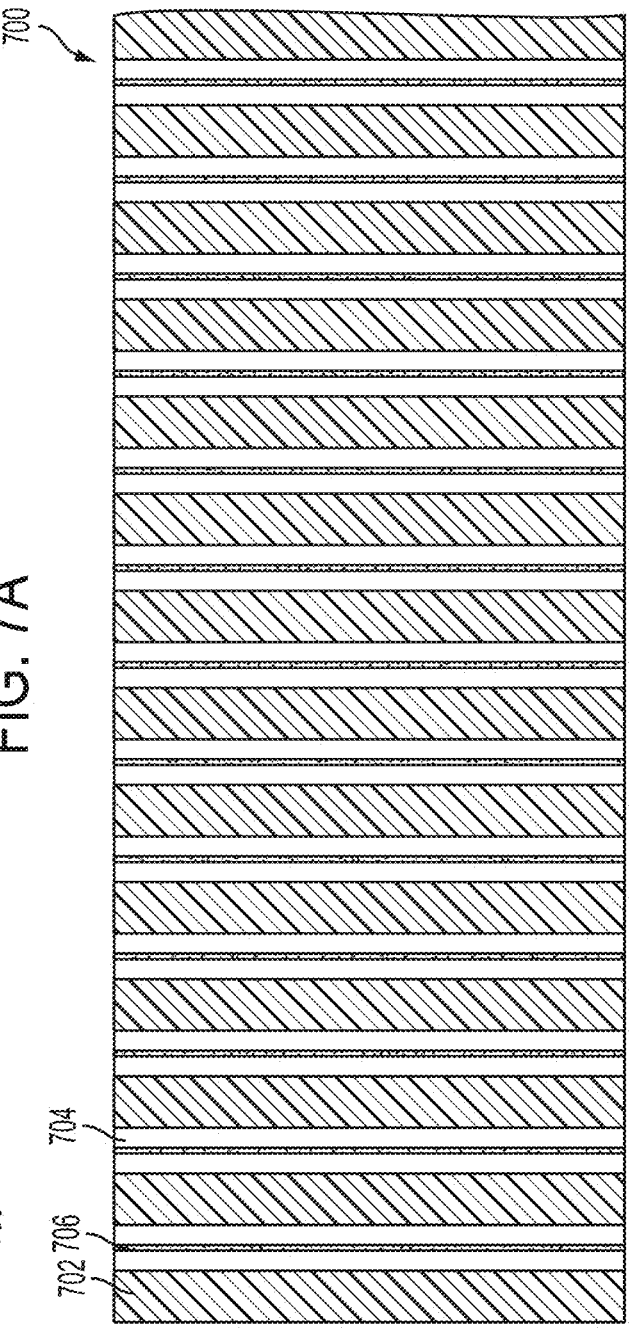
FIG. 7B is a top view of the adhesive layer of FIG. 7A.

The adhesive layer 100, shown in FIG. 1, provides the connecting interface between the device 100 and the user. An embodiment of the adhesive layer is shown in FIGS. 7A and 7B. The layer features thermally conductive material 702, adhesive 704 and wicking elements 706. The thermally conductive material 702 assists in the transfer of thermal energy from the user into the device 100. This provides a more efficient pathway through which heat may be directed into the device 100. Further, the device 100 may be designed such that the thermally conductive material 702 channels the thermal energy to a desired part of the device 100, such as the TEs of the thermal energy transfer layer 120.

An adhesive portion 704 of the layer 700 affixes the device 100 to the skin of the user. In the embodiment shown in FIGS. 7A and 7B, the adhesive coats the base of the polymer element 704. A wicking element 706 is also disposed in the adhesive portion 704. The element 706 assists in managing and transferring moisture exuded from the user. If the moisture was not managed and transferred away from the user's skin, user comfort and device affixment to the user could be compromised. The wicking element 706, as shown in the embodiment of FIGS. 7A and 7B, draws moisture away from the user's skin into the wicking element 706. The adhesive portion 704 may be constructed of hydrophilic material that helps conduct moisture through the layer. The moisture may then be transferred through the device 100, where it may be trapped or evaporated into the surrounding atmosphere. The adhesive used can be a number of potential temporary, skin safe adhesives. In the embodiment shown, the adhesive is a medical-grade adhesive used to affix medical devices and sensors to a user's skin temporarily. Alternatively, the adhesive may be a more permanent type.

Figure 8A:
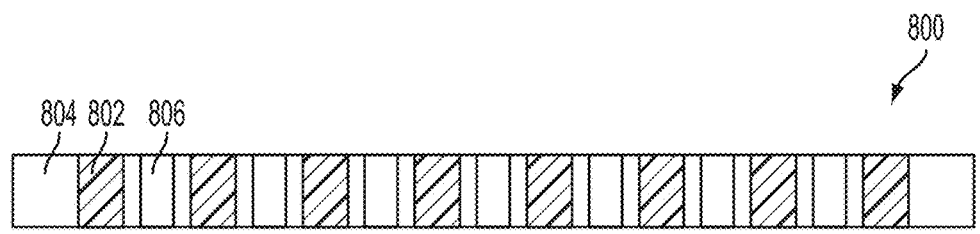
FIG. 8A is a cross-section of another example adhesive layer.
Figure 8B:
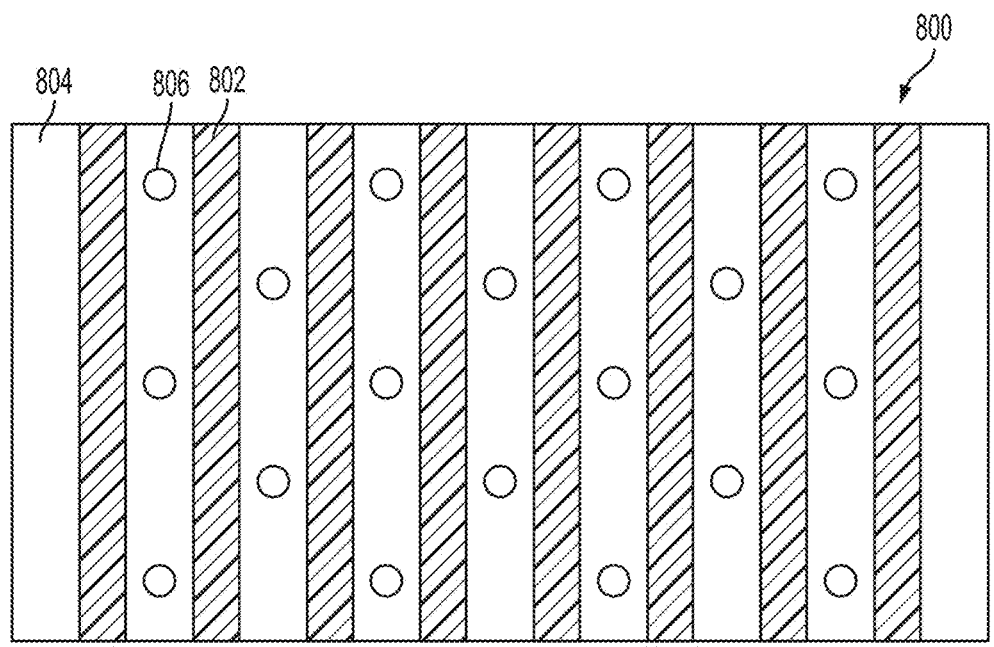
FIG. 8B is a top view of the adhesive layer of FIG. 8A.

Another embodiment of the adhesive layer is shown in FIGS. 8A and 8B. In this embodiment, the wicking elements 806 are holes. The holes 806 allow moisture to travel from the user's skin and into the device 100. Alternatively, the holes 806 may extend through the entire device 100. The moisture from the user's skin may be drawn through the holes 806 by capillary action. Alternatively, the moist vapor from the user can be exhausted through the holes 806 into the surrounding environment.

The adhesive portions 804 are interspersed with the thermally conductive material 802 as in the previous embodiment shown in FIGS. 7A and 7B.

Figure 9A:
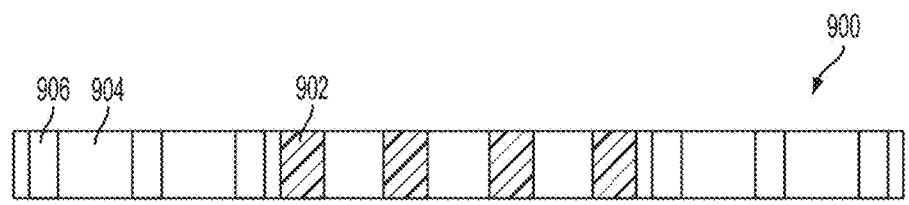
FIG. 9A is a cross-section of yet another example adhesive layer.
Figure 9B:
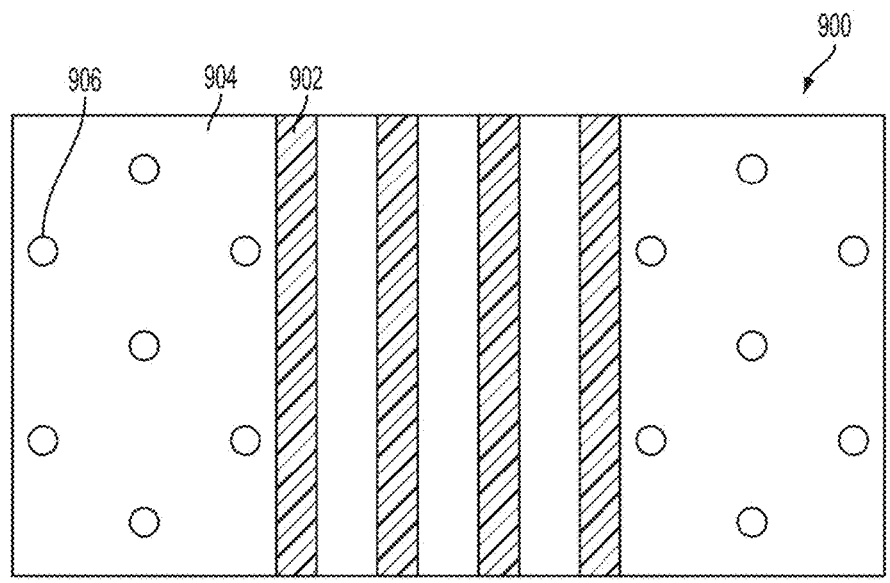
FIG. 9B is a top view of the adhesive layer of FIG. 9A.

Another embodiment of the adhesive layer is shown in FIGS. 9A and 9B. In this embodiment, the thermally conductive material 902 is concentrated under the TEs of the thermal energy transfer layer 130. This configuration channels the heat transferred from a user into the thermal energy transfer layer 130 thereby increasing user comfort. The adhesive portion 904 features the wicking elements 906. As with the previous embodiment, the wicking elements 906 are holes. The holes may extend through the adhesive layer or through the device.

Figure 10:
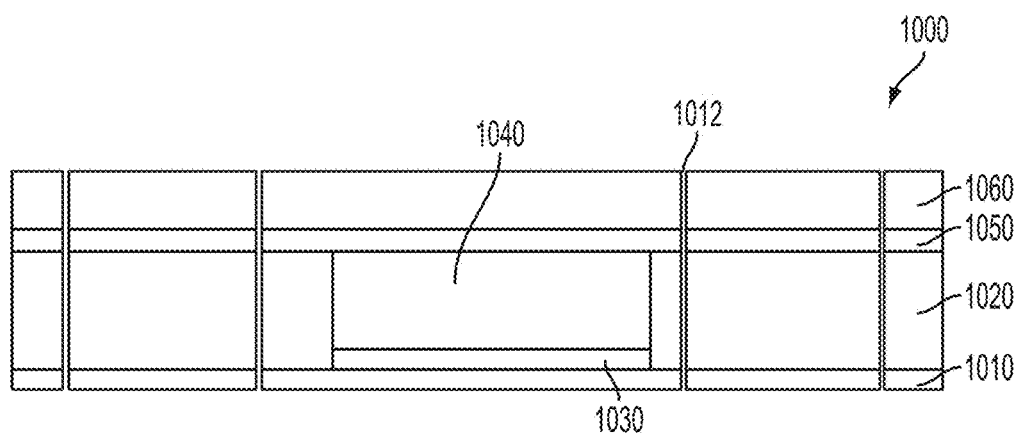
FIG. 10 is a cross section of another example active temperature control device.

FIG. 10 shows a cross-section of an alternative embodiment of the thermal regulation device 1000. The device is composed of an adhesive layer 1010 which has wicking pores 1012 that extend through the entire device 1000. The adhesive layer 1010 interfaces with and affixes the device 1000 to the user's skin. As with previous embodiments, the layer 1010 may contain thermally conductive material to assist with the conduction of thermal energy between the device 1000 and a user. The wicking pores 1012 assist in the removal of moisture from the user's skin. Trapped moisture may hinder the adhesives ability to affix the device 1000 to the user's skin and may decrease a user's comfort. The TEs and power circuitry in FGM are contained in the thermal energy transfer layer 1040, which is atop a thermal energy spreading layer 1030. The thermal energy spreading layer 1030 distributes the thermal energy from the user across the area of the TEs in the energy transfer layer 1040. Insulation 1020 surrounds the energy transfer layer 1040.

A second thermal energy spreading layer 1050 is atop the thermal energy transfer layer 1040. The second thermal energy spreading layer 1050 spreads the heat discharged from the energy transfer layer 1040. The spreading of heat through the layer 1050 allows more surface area to transfer thermal energy into the next layer, the thermal energy exchange layer, 1060. The thermal energy exchange layer 1060 has structures, similar to previous embodiments, which increase the surface area of the layer to better dissipate the thermal energy from the device 1000. The increased surface area of the layer 1060 increases the rate at which thermal energy may be convected from the surface. A protective layer, not shown, is disposed across the device 1000 that protects the layers from external damage. As in previous embodiments, the various layers of the device 1000 are flexible due to the use of polymeric and functionally graded materials.

Figure 11:
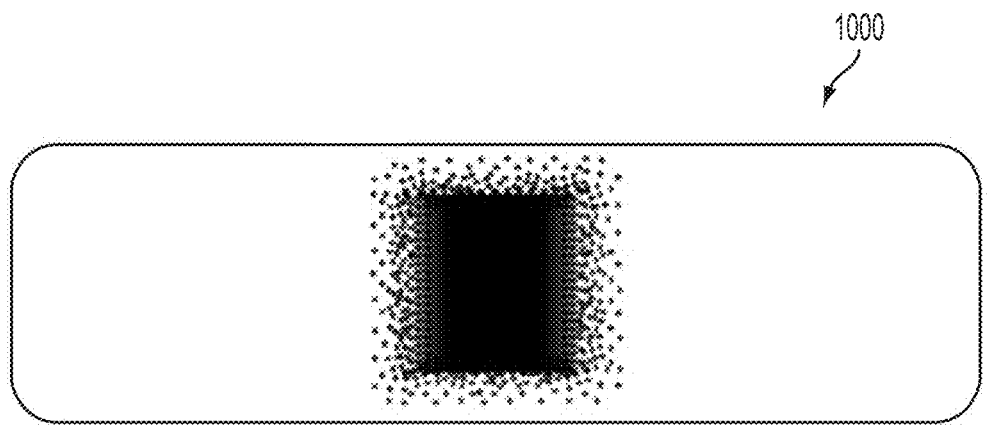
FIG. 11 is a top view of the thermoelectric elements of the device.

FIG. 11 illustrates a view of one thermoelectric conductor, showing the graded reinforcement decreasing in density the further away from the conductor. The changes in reinforcement agent, which may be particles made from material similar in composition to the thermoelectric conductor, increase the mechanical modulus of the surrounding material and create the grading to allow the structure to be flexible and stretchable.

Thermoelectric Interconnects

Figure 12:
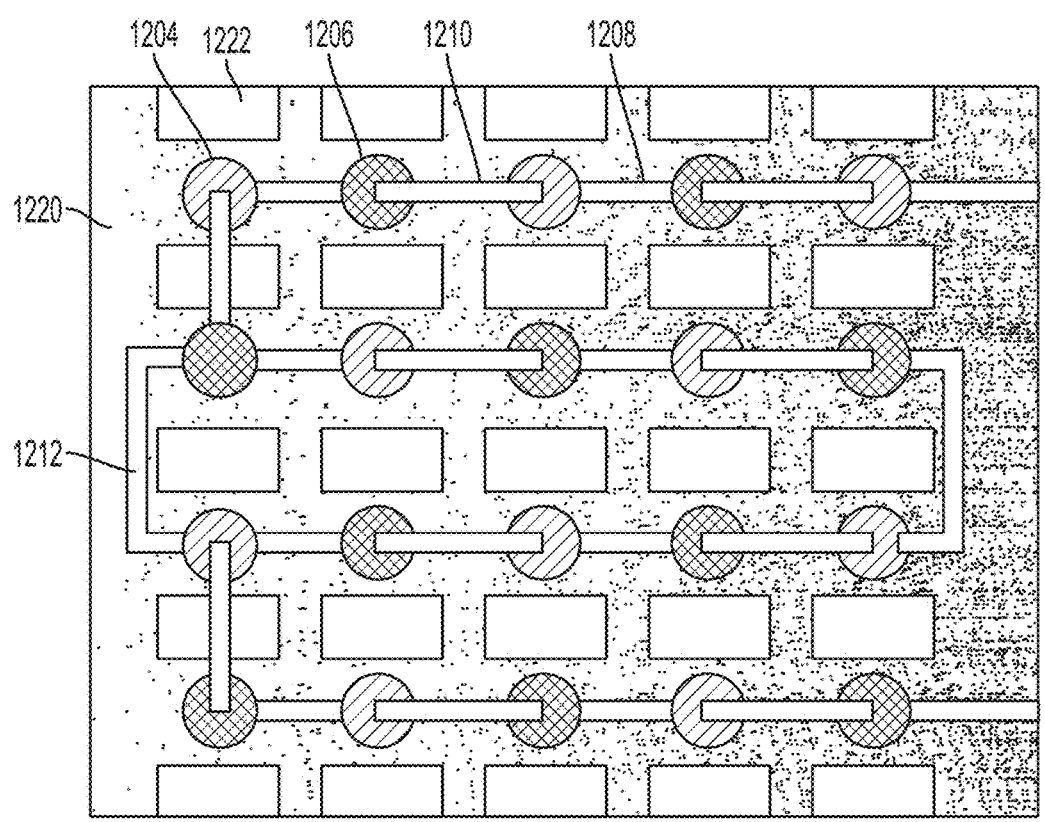
FIG. 12 is a top view showing example interconnected elements in a functionally graded material gradient.

FIG. 12 further illustrates the interconnection of the TEs 1204 and 1206 in the FGM matrix 1220. The top interconnect 1208 alternates with the upper interconnect 1210 in connecting the alternating TEs 1204 and 1206. The interconnect 1212 links the rows of the TEs, keeping the elements thermally parallel and electrically connected in series. The FGM 1220 is graded to be stiffer about the TEs and interconnects.

Figure 13:
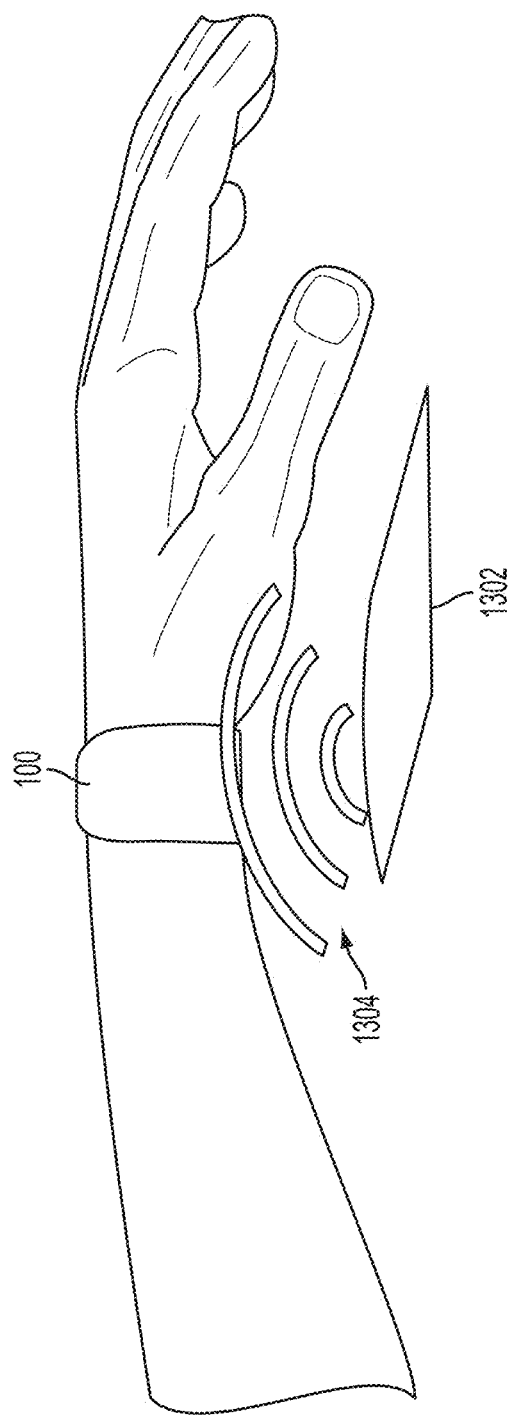
FIG. 13 shows a method of powering the device.

FIG. 13 illustrates a method of powering the device. In the embodiment shown, the device 100 is powered wirelessly using inductive power circuitry, such as inductive loop charging circuitry. The inductive power circuitry uses radiating power 1304 emitted from a source 1302 to power the device 100. One or more inductive charging base stations could be strategic placed in an environment in which one or more users are wearing one of the disclosed devices. As the users wearing the device nears one of the inductive charging base stations, the device is activated by the inductive charging loop and can optionally communicate with other base stations.

A user can set user-specific preferences through a user interface at a particular base station, which can command the network of base stations to power the user's device on and off according to the user-specific preferences. The base stations can also be used to collect data about the user(s) wearing the devices and/or the energy and temperature data in the environment in which the users and base stations interact.

Alternatively, the device 100 may be powered by a power source disposed on the device 100. The power source may be wired or wirelessly rechargeable, replaceable or not. In another embodiment, the device may be powered by electricity delivered by a wire or cord from an external source. Varying the supplied power to the device will vary the rate of thermal energy the TEs can transfer across themselves.

The flexible thermal management device is a flexible device that a user affixes to their skin. Once affixed, the unit uses active thermal management to remove thermal energy from a user. The powered thermoelectric elements create a temperature differential across their layer. The orientation of the temperature differential is determined by the flow of current through the thermoelectric elements. By creating the cool side of the thermoelectric elements oriented towards the user, the user's heat is drawn into the device and into the thermoelectric elements. The heat is then transferred to the outer side of the thermoelectric elements where it is dissipated through the thermal energy exchange layer that convects the extracted heat into the environment.

Alternatively, the direction of current flow through the TEs may be revered, which reverses the direction of the thermal differential. The reoriented thermal differential can then add thermal energy to the user, thereby warming the user.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A flexible active temperature control device, comprising:
    a thermal energy transfer layer having thermoelectric elements and a functionally-graded material integrated into a single layer, wherein the functionally graded material has a gradient, wherein the gradient has a decreasing density of particles farther away from the thermoelectric elements;
    a thermal energy spreading layer in thermal communication with the thermal energy transfer layer and configured to receive thermal energy from the thermal energy transfer layer and to spread the thermal energy through the thermal energy spreading layer; and
    a thermal energy exchange layer in thermal communication with the thermal energy spreading layer and configured to exchange the spread thermal energy with the thermal energy spreading layer.

2. The flexible active temperature control device of claim 1, further comprising an adhesive layer secured to the thermal energy exchange layer and configured to attach the device to a user's skin.

3. The flexible active temperature control device of claim 2, wherein the adhesive layer has a thermally conductive material disposed thereon, the thermally conductive material in thermal communication with the active thermal energy transfer layer and a user.

4. The flexible active temperature control device of claim 1, wherein the device is integrated into a user interface element structured to attach the device to a user's skin.

5. The flexible active temperature control device of claim 1, wherein the thermal energy spreading layer includes a polymeric matrix having thermally conductive particles disposed thereon and configured to spread thermal energy through the thermal energy spreading layer.

6. The flexible active temperature control device of claim 1, wherein the thermal energy spreading layer has a flexible heat pipe configured to spread the thermal energy through the thermal energy spreading layer.

7. The flexible active temperature control device of claim 1, wherein the thermal energy exchange layer has a textured, thermally-conductive polymer configured to exchange thermal energy with the thermal energy spreading layer.

8. The flexible active temperature control device of claim 1, wherein the thermal energy exchange layer includes a thermally conductive base having thermally conductive filled structures disposed thereon, the thermally conductive base is configured to exchange thermal energy with the thermal energy spreading layer.

9. The flexible active temperature control device of claim 1, further comprising a protective encapsulation secured to the thermal energy exchange layer and configured to protect the layers of the device.

10. The flexible active temperature control device of claim 1, further comprising at least one wicking element extending through a portion of a thickness of the device, the wicking element configured to transfer moisture away from a user's skin.

11. The flexible active temperature control device of claim 1, wherein the thermal energy transfer layer is disposed on a flexible heat pipe.

12. The flexible active temperature control device of claim 1, further comprising a power source electrically coupled to the thermoelectric elements and configured to supply power to the thermoelectric elements.

13. The flexible active temperature control device of claim 12, wherein the power source has inductive power circuitry configured to be powered by a source external to the device.

14. The flexible active temperature control device of claim 12, wherein the power source is disposed within the device.

15. A flexible active temperature control device, comprising:

a thermal energy transfer layer having thermoelectric elements and a functionally graded material integrated into a single layer, the functionally-graded material having a graded reinforcement in the thermal energy transfer layer, the graded reinforcement having a decreasing in density further away from the thermoelectric elements;

a thermal energy spreading layer in thermal communication with the thermal energy transfer layer and configured to receive thermal energy from the thermal energy transfer layer and to spread the thermal energy through the thermal energy spreading layer;

a thermal energy exchange layer in thermal communication with the thermal energy spreading layer and configured to exchange the spread thermal energy with the thermal energy spreading layer; and an adhesive layer secured to the thermal energy exchange layer and configured to attach the device to a user's skin, wherein the adhesive layer includes at least one wicking element extending through a portion of a thickness of the device, the wicking element configured to transfer moisture away from a user's skin.

* * * * *